(12) United States Patent
Schmenger et al.

(10) Patent No.: US 6,528,046 B1
(45) Date of Patent: Mar. 4, 2003

(54) CLEAR HAIR TREATMENT COMPOSITION

(75) Inventors: Juergen Schmenger, Weiterstadt (DE); Wilhelm Abels, Simi Valley, CA (US); Mehrdad Jahedshoar, Calabasas, CA (US)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 09/691,761

(22) Filed: Oct. 18, 2000

Related U.S. Application Data

(60) Provisional application No. 60/160,967, filed on Oct. 22, 1999.

(51) Int. Cl.[7] ................................................. A61K 7/06
(52) U.S. Cl. ................. 424/70.1; 424/70.11; 424/70.12
(58) Field of Search ............................ 424/70.1, 70.11, 424/70.12

(56) References Cited

U.S. PATENT DOCUMENTS

| | | | |
|---|---|---|---|
| 4,567,039 A | | 1/1986 | Stadnick et al. |
| 5,100,657 A | | 3/1992 | Ansher-Jackson et al. |
| 5,650,159 A | | 7/1997 | Lion et al. |
| 5,720,964 A | | 2/1998 | Murray |
| 5,876,463 A | | 3/1999 | Garcia et al. |
| 5,914,373 A | * | 6/1999 | Glancy et al. |
| 5,955,063 A | | 9/1999 | Brody et al. |
| 6,136,304 A | * | 10/2000 | Pyles |
| 6,153,570 A | | 11/2000 | Decoster |
| 6,159,914 A | | 12/2000 | Decoster et al. |

FOREIGN PATENT DOCUMENTS

| | | |
|---|---|---|
| WO | 96/40815 | 12/1996 |
| WO | 98/00494 | 1/1998 |
| WO | 98/00499 | 1/1999 |
| WO | 00/10508 | 3/2000 |

OTHER PUBLICATIONS

Schrader: "Grundanlagen Und Rezepturen Der Kosmetika", 2–Nd Edition, 1989, pp. 728–737.
E. Flick: "Cosmeti c and Toiletry Formulations" 2–Nd Edition, vol. 2, pp. 373FF (1989).
"International Ingredient Di ctionary and Handbook", 7–Th Edition, vol. 2, Se ction "Surfa ctants–Emulsifying Agents" (1997).

* cited by examiner

Primary Examiner—Thurman K. Page
Assistant Examiner—Humera N. Sheikh
(74) Attorney, Agent, or Firm—Michael J. Striker

(57) ABSTRACT

A hair-treating agent is described which is preferably in the form of an optically clear, transparent or translucent product and which contains (A) at least one hair-care silicone compound having at least one hydrophilic group, (B) at least one nonionic, amphiphilic associative thickener containing at least one hydrophilic group and optionally (C) at least one hair-care substance having at least one cationic group, in a cosmetically appropriate base. The agent is used as a leave-in hair treatment or as a hair rinse, thus conditioning the hair and conferring to it gloss and volume.

9 Claims, No Drawings

CLEAR HAIR TREATMENT COMPOSITION

This application claims the benefit of U.S. Provisional App. No. 60/160,967, Oct. 22, 1999.

BACKGROUND OF THE INVENTION

1. Field of the Invention

The object of the invention is a hair-treating agent useable particularly as leave-in hair-care agent or a hair rinse, preferably in the form of an optically clear product containing hydrophilic silicones and certain associative thickeners as well as, optionally, cationic hair-care substances.

2. Prior Art

As a rule, conventional hair-conditioning preparations, such as rinse-off or leave-on hair-care treatments are formulated on the basis of aqueous emulsions. Essential ingredients are cationic substances such as, for example, cationic surfactants, hydrophobic substances such as, for example, fatty alcohols and other oil components, emulsifiers and other specific agents and odorants. The most important ingredients are the cationic surfactants, fatty alcohols and emulsifiers. An overview of the formulation principles for hair-care rinses and hair-care agents can be found in Schrader, "Grundlagen und Rezepturen der Kosmetika" [Fundamentals and Formulations of Cosmetics], 2nd edition, 1989, pages 728 to 737. The main functions of conditioners are to provide an improvement in stylability, combability, gloss and feel of the treated hair. The treated hair often has a heavier and denser feel which is not always desirable. In addition, currently used oil-in-water [O/W] hair-care emulsions are normally milky-white and opaque. Desirable are products that are in an optically more attractive form and are clear, trans-parent or at least translucent. Various forms of clear hair-care agents are known and are described, for example, in E. Flick, "Cosmetic and Toiletry Formulations", 2nd edition, volume 2, pages 373 ff. These clear hair-care agents are based on polymers with a thickening action such as, for example, cellulose derivatives (tradenames Natrosol® and Methocel®), high-molecular-weight chitosan derivatives (tradename Kytamer® PC), complex polysaccharides (known as karaya gum and tragacanth or under the tradenames Jaguar® and Keltrol®) and acrylic acid polymers. All these described clear hair-care agents have the major drawback that the care effect is so weak that it does not even approach the effects of a conventional hair-care agent based on mixtures of fatty alcohols and quaternary surfactants. Hence, commercial sales of these clear hair-care agents known from the prior art are much lower than those of standard treatments.

SUMMARY OF THE INVENTION

Our objective was therefore to provide an agent meeting the typical conditioning requirements placed on hair conditioners and which at the same time is in an optically attractive form and confers to the hair less heaviness and a less dense feel than those resulting from a conventional hair-care agent.

We have now found that this objective can be met by use of a hair-treating agent having the composition described in the following. The object of the invention is a hair-treating agent containing (A) at least one hair-care silicone compound containing at least one hydrophilic group and (B) at least one nonionic, amphiphilic associative thickener in an appropriate cosmetic base.

Preferably, the agent according to the invention contains additionally a hair-care substance (C) containing at least one cationic group.

DESCRIPTION OF THE PREFERRED EMBODIMENTS

The agent meets very well the conditioning requirements placed on hair conditioners. After the treatment, the hair is noticeably smoother in both the wet and the dry state, and wet combability is markedly improved. Surprisingly, we have found that the thickener makes it possible to incorporate cationic substances and the said silicone compounds without the negative secondary properties of the thickener manifesting themselves. The technical properties of the agent according to the invention even exceed the properties of a conventional hair-care agent based on an aqueous emulsion of fatty alcohols and quaternary surfactants. Comparative tests carried out in hairdresser salons side-by-side on two halves of the scalp confirmed the better combability and natural hair feel conferred by the agent of the invention. The agent of the invention practically eliminated the negative, dull hair appearance imparted by fatty alcohol/cationic surfactant mixtures. The hair felt lighter and less dense. Moreover, the combination according to the invention makes it possible to prepare the agent in an optically attractive, clear formulation which in turn permits advantageous packaging in a transparent container, for example one made of glass or transparent plastic, for example polyethylene, polypropylene or polyethylene terephthalate.

The cationic substance (C) is contained in the agent according to the invention preferably in an amount from 0.01 to 10 wt % and particularly from 0.1 to 5 wt %, and it differs from silicone compounds (A) in that it contains no silicone units. The agent contains silicone compound (A) preferably in an amount from 0.01 to 10 wt % and particularly from 0.1 to 5 wt %, and the associative thickener (B) preferably in an amount from 0.1 to 5 wt % and particularly from 0.1 to 2 wt %.

The cationic substance (C) is a material which because of cationic or cationizable groups, particularly primary, secondary, tertiary or quaternary amino groups, exhibits substantivity to human hair. Suitable cationic substances are selected from among cationic surfactants, betaine-type surfactants, amphoteric surfactants, cationic polymers with cationic or cationizable groups, cationically derivatized proteins, cationically derivatized protein hydrolyzates and betaine.

Suitable cationic surfactants are surfactants containing a quaternary ammonium group. These surfactants can be of the cationic or of the amphoteric betaine type. Particularly preferred as cationic substance (C) are cationic surfactants. Suitable cationic surfactants contain amino groups or quaternized hydrophilic ammonium groups which in solution bear a positive charge and can be represented by general formula (I)

$$N^{(+)}R^1R^2R^3R^4 X^{(-)} \qquad (I)$$

wherein $R^1$ to $R^4$ independently of each other denote aliphatic, aromatic, alkoxy, polyoxyalkylene, alkylamido, hydroxyalkyl, aryl or alkaryl groups with 1 to 22 carbon atoms, and $X^{(-)}$ stands for an anion, for example a halogen, acetate, phosphate, nitrate or alkylsulfate, and preferably a chloride. Besides the carbon atoms and hydrogen atoms, the aliphatic groups can also contain linking groups or other groups, for example hydroxyl or additional amino groups.

Examples of suitable cationic surfactants are the chlorides or bromides of alkyldimethylbenzylammonium salts, alkyltrimethylammonium salts, for example cetyltrimethylammonium chloride or bromide, tetradecyltrimethylammonium chlorides or bromides, alkyldimethylhydroxyethylammonium chlorides or bromides, dialkyldimethylammonium chlorides or bromides, alkylpyridinium salts, for example laurylpyridinium or cetylpyridinium chloride, alkylamidoethyl trimethylammonium ether sulfates, as well as compounds with a cationic character, such as amine oxides, for example alkylmethyl-amine oxides or alkylaminoethyidimethylamine oxides. Particularly preferred is cetyltrimethylammonium chloride which, for example in the form of a 26% aqueous solution, is marketed by Henkel KGaA, Düsseldorf, Germany, under the tradename Dehyquart®, by Hoechst AG, Frankfurt, Germany, under the tradename Genamin® CTAC, and in the form of a 50% solution in isopropanol by Akzo Chemicals GmbH, Düren, Germany, under the tradename Arquat® 16-50.

Suitable amphoteric surfactants are the derivatives of aliphatic quaternary ammonium, phosphonium and sulfonium compounds having formula (II)

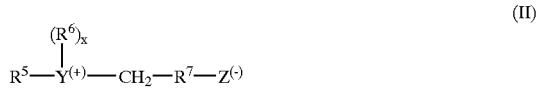

(II)

wherein $R^6$ denotes a straight-chain or branched alkyl, alkenyl or hydroxyalkyl group with 8 to 18 carbon atoms, 0 to about 10 ethylene oxide units and 0 to 1 glycerol unit; Y denotes an N—, P— or S— containing group; $R^6$ denotes an alkyl or monohydroxyalkyl group with 1 to 3 carbon atoms; x equals 1 when Y is a sulfur atom and it equals 2 when Y is a nitrogen or phosphorus atom; $R^7$ denotes an alkylene or hydroxyalkylene group with 1 to 4 carbon atoms, and $Z^{(-)}$ denotes a carboxylate, sulfate, phosphonate or phosphate group.

Other amphoteric surfactants such as the betaines are also suitable for the hair-treating agent of the invention. Examples of betaines include C8 to C18 alkylbetaines such as cocodimethylcarboxy-methylbetaine, lauryldimethylcarboxymethylbetaine, lauryidimethyl-α-carboxyethylbetaine, cetyl-dimethylcarboxymethylbetaine, oleyldimethyl-γ-carboxypropylbetaine and laurylbis-(2-hydroxypropyl)-α-carboxyethylbetaine; C8 to C18 sulfobetaines, such as cocodimethylsulfopropylbetaine, stearyldimethylsulfopropylbetaine, lauryldimethylsulfoethylbetaine, laurylbis-(2-hydroxyethyl) sulfopropylbetaine; the carboxyl derivatives of imidazole, the $C_8$ to $C_{18}$ alkyldimethylcarbonylmethyl-ammonium salts and the C8 to C18 fatty acid alkylamidobetaines, for example the cocofatty acid amidopropylbetaine which, for example in the form of a 30% aqueous solution, is marketed by Goldschmidt AG under the tradename Tego® Betain L7, and the N-coco fatty acid amidoethyl-N-[2-(carboxymethoxy)ethyl]glycerol (CTFA[1] name: cocoamphocarboxyglycinate) which, for example in the form of a 50% aqueous solution, is sold by Miranol Chemical Co. under the tradename Miranol® C2M.

The suitable cationic polymers are preferably hair-strengthening or hair-conditioning polymers. Suitable polymers of component (C) preferably contain quaternary amino groups. The cationic polymers can be homopolymers or copolymers, with the quaternary nitrogen-containing groups being present either in the polymer chain or, preferably, as substituents on one or more of the monomers. The ammonium groups-containing monomers can be copolymerized with noncationic monomers. Suitable cationic monomers are unsaturated compounds undergoing free radical-induced polymerization and which bear at least one cationic group, particularly ammonium-substituted vinyl monomers, for example trialkylmethacryloxyalkylammonium, trialkylacryloxyalkylammonium, dialkyldiallylammonium, and quaternary vinylammonium monomers with cyclic, cationic, nitrogen-containing groups such as pyridinium or imidazolium or quaternary pyrrolidones, for example alkylvinylimidazolium, alkylvinylpyridinium or alkylvinylpyrrolidone salts. The alkyl groups of these monomers are preferably lower alkyl groups such as, for example C1 to C7 alkyl groups, and particularly C1 to C3 alkyl groups.

The ammonium groups-containing monomers can be copolymerized with noncationic monomers. Suitable comonomers are, for example, acrylamide, methacrylamide, alkyl and dialkylacrylamide, alkyl and dialkylmethacrylamide, alkyl acrylate, alkyl methacrylate, vinylcaprolactone, vinylcaprolactam, vinylpyrrolidone, vinyl esters, for example vinyl acetate, furthermore vinyl alcohol, propylene glycol, or ethylene glycol, the alkyl groups of these monomers preferably being C1 to C7 alkyl groups and particularly C1 to C3 alkyl groups.

Suitable polymers with quaternary amino groups are, for example, the polymers found in the CTFA Cosmetic Ingredient Dictionary under the designation Polyquaternium, such as methylvinylimidazolium chloride/vinylpyrrolidone copolymer (Polyquaternium 16) or the quaternized vinylpyrrolidone/dimethylaminoethyl methacrylate copolymer (Polyquaternium 11).

Suitable among the cationic polymers that can be present in the agent of the invention is, for example, vinylpyrrolidone/dimethylaminoethyl methacrylate methosulfate copolymer, marketed by Gaf Co., USA, under the tradenames Gafquat® 755 N and Gafquat® 734, of which Gafquat® 734 is particularly preferred. Other suitable cationic polymers are, for example, LUVIQUAT® HM 550, a copolymer of polyvinylpyrrolidone and imidazolium methochloride, marketed by BASF, Germany, Merquat® Plus 3300, a terpolymer of dimethyldiallylammonium chloride, sodium acrylate and acrylamide, marketed by Calgon, USA, Gaffix® VC 713, a terpolymer of vinylpyrrolidone, dimethylaminoethyl methacrylate and vinylcaprolactam, marketed by ISP, USA, and Gafquat® HS 100, a vinylpyrrolidone/methacrylamidopropyltrimethylammonium chloride copolymer marketed by GAF.

Suitable cationic polymers derived from natural polymers are the cationic derivatives of polysaccharides, for example cationic derivatives of cellulose, starch or guar. Also suitable are chitosan and chitosan derivatives. Cationic polysaccharides have the general formula (III)

(III)

wherein

G denotes an anhydroglucose group, for example starch- or cellulose anhydroglucose;

B denotes a divalent linking group, for example an alkylene, oxyalkylene, polyoxyalkylene or hydroxyalkylene group;

$R^a$, $R^b$ and $R^c$ independently of each other denote alkyl, aryl, alkylaryl, arylakyl, alkoxyalkyl or alkoxy-aryl groups, each with up to 18 carbon atoms, the total number of carbon atoms in $R^a$, $R^b$ and $R^c$ preferably amounting to a maximum of 20;

$X^{(-)}$ is a common counterion with the same meaning as in formula (I) and preferably is a chloride.

A cationic cellulose is marketed by Amerchol under the commercial name Polymer JR and has the INCI[2] name Polyquaternium 10. Another cationic cellulose has the INCI name Polyquaternium 24 and is marketed by Amerchol under the commercial name Polymer LM 200. A suitable cationic guar derivative has the INCI designation Guar Hydroxypropyltrimonium Chloride and is marketed under the tradename Jaguar® R.

Particularly preferred cationic substances are chitosan, chitosan salts and chitosan derivatives. The chitosans used according to the invention are completely or partly deacetylated chitins. The preferred starting material for preparing chitosan is the chitin contained in the shell wastes of crustaceans which are available in large amounts as an inexpensive, natural raw material. The molecular weight of chitosan can be distributed over a broad range, for example from 20,000 to about 5 million g/mole.

Suitable is, for example, a low-molecular-weight chitosan with a molecular weight of 30,000 to 70,000. Preferably, the molecular weight exceeds 100,000 g/mole, a molecular weight of 200,000 to 700,000 being particularly preferred. The degree of deacetylation is preferably from 10 to 99% and particularly from 60 to 99%.

A suitable chitosan is sold, for example, by Kyowa Oil & Fat, Japan, under the tradename Flonac®. It has a molecular weight of 300,000 to 700,000 and is 70–80% deacetylated. A preferred chitosan salt is chitosonium pyrrolidonecarboxylate, sold, for example, by Amerchol, USA, under the tradename Kytamer PC. The chitosan it contains has a molecular weight of about 200,000 to 300,000 g/mole and is 70–85% deacetylated. Suitable chitosan derivatives are the quaternized, alkylated or hydroxyalkylated derivatives, for example hydroxyethylchitosan or hydroxybutylchitosan.

The chitosans or chitosan derivatives are preferably used in neutralized or partly neutralized form. The degree of neutralization of the chitosan or chitosan derivative is preferably at least 50% and particularly between 70 and 100%, based on the number of free base groups. In principle, all cosmetically tolerated inorganic or organic acids can be used as neutralization agents, among others, for example formic, tartaric, malic, lactic, citric, pyrrolidonecarboxylic or hydrochloric acid, among which pyrrolidonecarboxylic acid is preferred.

Other suitable cationic hair-care compounds are the cationically modified protein derivatives or cationically modified protein hydrolyzates, for example those known under the INCI names Lauryidimonium Hydroxypropyl Hydrolyzed Wheat Protein, Lauryidimonium Hydroxypropyl Hydrolyzed Casein, Lauryidimonium Hydroxypropyl Hydrolyzed Collagen, Lauryidimonium Hydroxypropyl Hydrolyzed Keratin, Lauryidimonium Hydroxypropyl Hydrolyzed Silk, Lauryidimonium Hydroxypropyl Hydrolyzed Soy Protein or Hydroxypropyltrimonium Hydrolyzed Wheat, Hydroxypropyltrimonium Hydrolyzed Casein, Hydroxypropyltrimonium Hydrolyzed Collagen, Hydroxypropyltrimonium Hydrolyzed Keratin, Hydroxypropyltrimonium Hydrolyzed Rice Bran Protein, Hydroxypropyltrimonium Hydrolyzed Silk, Hydroxypropyltrimonium Hydrolyzed Soy Protein and Hydroxypropyltrimonium Hydrolyzed Vegetable Protein.

Suitable cationically derivatized protein hydrolyzates are mixtures of substances obtainable, for example, by reaction of proteins hydrolyzed under alkaline or acidic conditions or enzymatically, with glycidyltrialkylammonium salts or 3-halo-2-hydroxypropyltrialkylammonium salts. Proteins serving as starting materials for the protein hydrolyzates can be of either vegetable or animal origin. Common starting materials are, for example, keratin, collagen, elastin, soy protein, rice protein, milk protein, wheat protein, silk protein or almond protein. Hydrolysis produces mixtures of substances with molecular weights ranging from about 100 to about 50,000. Common average molecular weights range from about 500 to about 1000. Advantageously, the cationically derivatized protein hydrolyzates contain one or two long C8 to C22 alkyl chains and correspondingly two or one short C1 to C4 alkyl chains. Compounds containing one long chain are preferred.

The hydrophilic groups of the hair care silicone compounds (A) used according to the invention are preferably selected from among hydroxyl groups, primary, secondary or tertiary amino groups and quaternary ammonium, alkylene oxide, betaine and thiosulfate groups.

Suitable and particularly preferred are cationic silicone compounds. These bear cationic or cationizable substituent groups. Suitable cationic silicone compounds contain at least one amino group or at least one ammonium group. Suitable silicone polymers are known under the INCI name Amodimethicones. These are polydimethylsiloxanes with aminoalkyl groups. The aminoalkyl groups can be present as side groups or end groups. Suitable aminosilicones have the general formula (IV)

wherein

R[8], R[9], R[14] and R[15] independently of each other are equal or different and denote C1 to C10 alkyl, phenyl, hydroxyl, hydrogen, C1 to C10 alkoxy or acetoxy, preferably C1 to C4 alkyl and particularly methyl;

R[10] and R[16] independently of each other are equal or different and denote —$(CH_2)_a$—$NH_2$ where a equals 1 to 6, C1 to C10 alkyl, phenyl, hydroxy, hydrogen, C1 to C10 alkoxy or acetoxy, preferably C1 to C4 alkyl and particularly methyl;

R[11], R[12] and R[13] independently of each other are equal or different and denote hydrogen, C1 to C20 hydrocarbon which can contain O or N atoms, preferably C1 to C10 alkyl or phenyl, particularly C1 to C4 alkyl and especially methyl;

Q denotes —A—$NR^{17}R^{18}$ or —A—$N^+R^{17}R^{18}R^{19}$, wherein A stands for a divalent C1 to C20 alkylene linking group possibly also containing O or N atoms or OH groups, and R[17], R[18] and R[19] independently of each other are equal or different and denote hydrogen or C1 to C22 hydrocarbon, preferably C1 to C4 alkyl or phenyl. Q preferably stands for —$(CH_2)_3$—$NH_2$, —$(CH_2)_3NHCH_2CH_2NH_2$, —$(CH_2)_3OCH_2CHOHCH_2NH_2$, —$(CH_2)_3N(CH_2CH_2OH)_2$, —$(CH_2)_3$—$NH_3^+$ and $(CH_2)_3OCH_2CHOHCH_2N^+(CH_3)_2R^{20}$, wherein R[20] denotes a C1 to C22 alkyl group possibly also containing OH groups; x denotes a numeral from 1 to 10,000 and preferably from 1 to 1000, and y denotes a numeral from 1 to 500 and preferably from 1 to 50.

The molecular weight of aminosilicones is preferably between 500 and 100,000. The amine part (meq/g) preferably ranges from 0.05 to 2.3 and particularly from 0.1 to 0.5.

Suitable silicone polymers with two terminal quaternary ammonium groups are known under the INCI name Quaternium 80. These are dimethylsiloxanes with two terminal aminoalkyl groups. Suitable quaternary aminosilicones have the general formula (V)

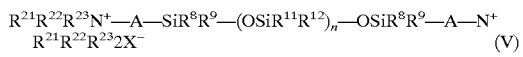

$$R^{21}R^{22}R^{23}N^{+}-A-SiR^{8}R^{9}-(OSiR^{11}R^{12})_n-OSiR^{8}R^{9}-A-N^{+}R^{21}R^{22}R^{23}2X^{-} \quad (V)$$

wherein

A has the same meaning as in the foregoing formula (IV) and preferably denotes —(CH$_2$)$_3$CH$_2$CHOHCH$_2$N$^+$(CH$_3$)$_2$R$^{20}$, R$^{20}$ standing for a C1 to C22 alkyl group possibly containing OH groups;

R$^8$, R$^9$, R$^{11}$ and R$^{12}$ have the same meaning as in the foregoing formula (IV) and preferably denote methyl;

R$^{21}$, R$^{22}$ and R$^{23}$ independently of each other denote C1 to C22 alkyl groups possibly containing hydroxyl groups and wherein preferably at least one of the groups has 10 carbon atoms and the remaining groups have 1 to 4 carbon atoms, and n is a numeral from 0 to 200 and preferably from 10 to 100. Such diquaternary polydimethylsiloxanes are marketed by GOLDSCHMIDT, Germany, under the tradenames Abil® Quat 3270, 3272 and 3274.

Suitable silicones with alkylene oxide groups are polydimethylsiloxanes with polyoxyalkylated substituents, particularly silicones modified with polypropylene oxide, polyethylene oxide or a mixture thereof. In this case, the alkylene oxide groups can be lateral or terminal, and the polymers can be polydimethylsiloxane/polyalkylene oxide block copolymers. The alkylene oxide-modified siloxanes are also known as dimethylsiloxane glycol copolymers or as Dimethicone Copolyols. Suitable silicones with hydroxyl groups are the Dimethiconols. These are polydimethylsiloxanes with hydroxyl end groups. Suitable silicones with thiosulfate groups are known under the INCI name Dimethicone/Sodium PG-Propyldimethicone Thiosulfate Copolymer.

The nonionic amphiphilic associative thickener (B) is a polymer containing both hydrophilic and hydrophobic groups. Associative thickeners are water-soluble polymers containing surfactant-like hydrophobic moieties which, in a hydrophilic, particularly aqueous medium, are capable of associating, namely interacting, with themselves as well as with other hydrophobic substances. The resulting associative network then causes the medium to thicken or to gel. Typically, associative thickeners are made by polymerization of a polyethylene oxide prepolymer and an at least difunctional, polyconden-sable substance, for example an isocyanate, whereby monohydric alcohols or diols with large aryl, alkyl or aryl/alkyl groups are incorporated to produce the hydrophobic modification. Thus, preferred associative thickeners are hydrophobically modified polyalkylene glycols. In this case, the hydrophilic moiety consists of polyoxyalkylene units, preferably polyoxyethylene, but also polyoxypropylene, units or a mixture thereof. The hydrophobic moiety preferably consists of hydrocarbon groups, for example long-chain alkyl, alkylaryl or arylalkyl groups.

Particularly preferred associative thickeners are hydrophobically modified aminoplast polyether copolymers. For the structure and preparation of said copolymers, the reader is referred to WO 96/40815. WO 96/40815 describes water-dispersible or water-soluble copolymers which are reaction products of acid-catalyzed polycondensation of at least difunctional aminoplast monomers, at least difunctional alkylene polyethers and monofunctional compounds with hydrophobic groups. Suitable aminoplasts are shown in FIG. 1 of WO/40815. Particularly preferred are the glycol uril derivatives of formula X in WO 96/40815. Suitable alkylene polyethers are shown in FIG. 2 of WO 96/40815. Preferred alkylene polyethers are the polyethylene oxide diols. These can have a degree of ethoxylation from 20 to 500, preferably from 50 to 350 and particularly from 100 to 250. Suitable monofunctional compounds with hydrophobic groups are those of formula XIV in WO 96/40815.

Suitable associative thickeners of the invention are selected from polymers of general formula (VI)

wherein

Amp denotes an aminoplast monomer or a radical of an aminoplast oligomer or aminoplast polymer, AO denotes an alkylene oxide group, R denotes hydrogen, C1 to C4 alkyl or C1 to C4 acyl, and x and y are numerals greater than 1.

Particularly preferred are the reaction products of the acid-catalyzed polycondensation of (a) glycol urils of general formula (VII)

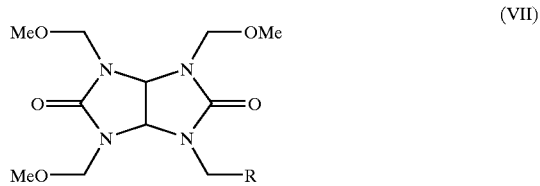

wherein R stands for H or preferably for OMe, (b) a polyethylene oxide diol with a degree of ethoxylation from 20 to 500, preferably from 50 to 350 and particularly from 100 to 250, and (c) an optionally ethoxylated hydrophobic alcohol, alkylphenol, thiol, carboxamide, carbamate or a hydrophobic carboxylic acid, as described on pages 17 to 19 of WO 96/40815. A particularly preferred glycol uril is 1,3,4,6-tetramethoxymethylglycol uril.

Suitable associative thickeners are those bearing the INCI names Polyether 1, PEG 180/Octoxynol 40/TMMG Copolymer and PEG 180/Laureth 50/TMMG Copolymer. These thickeners are sold by Süd Chemie under the tradenames Pure-Thix® HH, L and M.

The agent according to the invention is preferably produced in an aqueous or aqueous-alcoholic medium and is characterized, in particular, by its clarity and transparency. For this reason, the agent is advantageously marketed in an optically attractive package made of transparent or translucent material. Suitable packaging materials are, in particular, glass and transparent or translucent plastics, for example polyethylene terephthalate. Suitable alcohols are, in particular, the lower alcohols with 1 to 4 carbon atoms commonly used for cosmetic purposes, for example ethanol and isopropanol. The water content is preferably from 40 to 95 wt % and particularly from 60 to 90 wt %. The alcohol content is preferably from 1 to 30 wt % and particularly from 5 to 20 wt %. Other, particularly preferred water-soluble solvents or humectants are the polyhydric alcohols, particularly those with 2 to 4 carbon atoms, for example glycerol, ethylene glycol or propylene glycol, used in an amount from 0.1 to 10 wt % and preferably from 0.5 to 5 wt %. Purely aqueous formulations are particularly preferred.

In a preferred embodiment, the agent according to the invention contains additionally at least one nonionic surfactant. Suitable nonionic surfactants are, for example, the nonionic surfactants indicated in the "International Cosmetic Ingredient Dictionary and Handbook", 7th edition, vol. 2, section on "Surfactants-Emulsifying Agents". Suitable nonionic surfactants are preferably selected from among ethoxylated fatty acids with 10 to 26 carbon atoms, ethoxylated monohydric or polyhydric alcohols with 1 to 6 carbon atoms, ethoxylated fatty alcohols with 10 o 26 carbon atoms, ethoxylated hydrogenated or non-hydrogenated castor oil, alkylpolyglucosides, glyceride alkoxylates, fatty acid glyceride polyalkylene glycol ethers of fatty acid partial glyceride polyalkylene glycol ethers, each with less than 30 alkylene glycol units, for example polyethylene glycol (7) glyceryl cocoate, polyglycol amides, fatty acid sugar esters, ethoxylated fatty acid sugar esters and partial glycerides. The degree of ethoxylation of ethoxylated surfactants is usually from 1 to 400, preferably from 2 to 200 and particularly from 3 to 25.

In a preferred embodiment, the agent of the invention contains only water-soluble surfactants and emulsifiers, namely surfactants which at a concentration of 1 wt % in water at 20° C. give a clear solution.

Preferred nonionic surfactants are, in particular, the fatty alcohol ethoxylates. Suitable are, for example, alcohols with 10 to 18 and preferably 10 to 16 carbon atoms and a degree of ethoxylation of preferably 2 to 200 and particularly 3 to 25. The additional nonionic surfactants are preferably used in an amount from 0.01 to 5 wt %.

In another preferred embodiment, the agent of the invention contains additionally at least one film-forming, hair-strengthening, synthetic or natural polymer. This additional polymer can be of a nonionic, anionic or amphoteric nature and is preferably used in an amount from 0.5 to 10 wt %. By film-forming, hair-strengthening polymers are meant polymers which when applied in the form of a 0.1 to 5% aqueous, alcoholic or aqueous-alcoholic solution are capable of strengthening hair by depositing a polymer film on it.

Furthermore, the agent according to the invention can contain the common constituents used in hair-treating agents, for example non-strengthening nonionic polymers, non-strengthening anionic polymers and non-strengthening natural polymers as well as combinations thereof, preferably in an amount from 0.01 to 10 wt %; perfumes preferably in an amount from 0.01 to 5 wt %; wetting agents or emulsifiers from the classes of anionic, cationic, amphoteric or nonionic surface-active substances, preferably in an amount from 0.01 to 10 wt %; humectants; preservatives, bactericides and fungicides, for example 2,4,4-trichloro-2-hydroxydiphenyl ether [sic-Translator], parabens [p-hydroxybenzoic acids] or methylchloroisothazolinone, in an amount from 0.01 to 1.0 wt %; buffers, for example sodium citrate or sodium phosphate, in an amount from 0.1 to 1.0 wt %; colorants, for example fluorescein sodium salt, in an amount from about 0.1 to 1.0 wt %; hair-care agents, for example plant and herb extracts, protein and silk hydrolyzates or lanolin derivatives, in an amount from 0.1 to 5 wt %; sunscreen agents, antioxidants, free radical scavengers, antidandruff agents, fatty alcohols, glossing agents, vitamins and scalp oil replacing agents, used in an amount from 0.1 to 10 wt %.

The agent according to the invention can have a pH from 2.0 to 9.5. Particularly preferred are weakly acidic values from 4.5 to 7 and particularly from 5.5 to 9.5. When the agent according to the invention is in the acidic range, it can contain organic or inorganic acids, for example formic, tartaric, malic, maleic, fumaric, glyoxylic, pyrrolidonecarboxylic, citric, lactic, sulfuric, acetic, hydrochloric or phosphoric acid among others.

The agent can be in the form of a lotion, thickened lotion, liquid or highly viscous gel. It is preferably in a medium-viscous form, in other words it preferably has the consistency of a thickened lotion or liquid. When it is in a low-viscous form, it can also be sprayed onto the hair thus becoming very well distributed. In this case, the hair-treating agent according to the invention is used in combination with an appropriate mechanically actuated spraying device. By mechanically actuated spraying device is meant a device which makes it possible to spray a liquid without the use of a propellant. A suitable mechanical spraying device is, for example, a spray pump or an elastic container provided with a spray valve and which is filled with the cosmetic agent of the invention under pressure. The pressure causes the elastic container to expand. When the spray valve is opened, the elastic container contracts and the agent is released continuously.

The agent of the invention is used by applying it into or onto dry hair or, after the hair was washed, wet or moist hair in an amount sufficient for the desired conditioning effect. The amount used depends on hair fullness and typically ranges from 1 to 25 grams. For the preferred use of the agent as a rinse product, the hair is rinsed after a sufficient exposure time of, for example, 1 to 15 minutes. The hair is then optionally combed out, styled and dried. When the agent is used as a leave-in product, the hair is not rinsed after the agent has been applied.

The following examples illustrate the invention further.

EXAMPLE 1

| | Clear Hair-Care Agent for Damaged Hair |
|---|---|
| 3.0 g | of Arquad ® 12-25 (25%, Lauryltrimonium Chloride) |
| 2.0 g | of Abil ® 9950 (30%, Dimethicone Propyl PG Betaine) |
| 1.1 g | of Pure Thix ® HH (Polyether 1, 20% in butylene glycol/water) |
| 0.5 g | of Brij ® 30 (Laureth 4) |
| to 100 g | water |

EXAMPLE 2

| | Clear Hair Rinse for Permanently Waved Hair |
|---|---|
| 1.0 g | of Arquad ® 12-25 (25%, Lauryltrimonium Chloride) |
| 0.6 g | of Tegobetain ® (30% in water, cocoamidopropylbetaine) |
| 0.8 g | of Abil ® Quat 3272 (50% in propylene glycol, Quaternium 80, diquaternary silicone) |
| 0.8 g | of Pure Thix ® L (PEG 180/Octoxynol 40/TMMG copolymer) |
| 0.2 g | of glyoxylic acid |
| to 100 g | water |

EXAMPLE 3

| | Clear Leave-in Treatment |
|---|---|
| 1.0 g | of Tallowtrimonium Chloride |
| 2.0 g | of Abil ® S 201 (30% in isopropanol/water), Dimethicone/sodium PG Propyldimethicone Thiosulfate Copolymer) |
| 1.1 g | of Pure Thix ® M (PEG 180/Laureth 50/TMMG copolymer) |
| 3.0 g | of Luviquat ® FC 905 (40% in water, Polyquaternium 16) |
| to 100 g | water |

EXAMPLE 4

| Clear Hair-Care Agent for Untangling Hair | |
|---|---|
| 2.5 g | of Arquad ® 12-50 (50%, Lauryltrimonium Chloride) |
| 1.8 g | of Abil ® Quat 3270 (50% in propylene glycol, Quaternium 80, diquaternary silicone) |
| 1.3 g | of Pure Thix ® HH (20% in butylene glycol/water) |
| 0.3 g | of Brij ® 30 (Laureth 4) |
| 0.2 g | of citric acid |
| to 100 g | water |

EXAMPLE 5

| Clear Hair Rinse Unusually Gentle | |
|---|---|
| 0.8 g | of Arquad ® 12-25 (25%, Lauryltrimonium Chloride) |
| 1.0 g | of Dow Corning ® 193 (Dimethicone Copolyol) |
| 1.0 g | of Pure Thix ® M (PEG 180/Laureth 50/TMMG copolymer) |
| 0.5 g | of Rewoteric ® AM CAS (50% in water, cocoamidopropyl hydroxysultaines) |
| to 100 g | water |

EXAMPLE 6

| Clear Leave-in Treatment | |
|---|---|
| 1.0 g | of Arquad ® 12-25 (25%, Lauryltrimonium Chloride) |
| 2.0 g | of Abil ® 8863 (Dimethicone Copolyol) |
| 0.9 g | of Pure Thix ® HH (20% in butylene glycol/water) |
| 0.5 g | of Luviskol ® K30 (polyvinylpyrrolidone) |
| to 100 g | water |

We claim:

1. A clear hair-treating agent comprising
at least one hair-care silicone compound having at least one hydrophilic group;
at least one nonionic, amphiphilic associative thickener selected from the group consisting of hydrophobically modified aminoplast/polyether copolymers; and
a cosmetic base containing water, said at least one hair-care silicone compound and said at least one nonionic, amphiphilic associative thickener;
wherein said at least one hydrophilic group of said at least one hair-care silicone compound is selected from the group consisting of hydroxyl groups, primary amino groups, secondary amino groups, tertiary amino groups, quaternary ammonium groups, alkylene oxide groups, betaine groups and thiosulfate groups.

2. The hair-treating agent according to claim 1, further comprising a hair-care substance having at least one cationic group.

3. The hair-treating agent according to claim 2, wherein said hair-care substance is selected from the group consisting of cationic surfactants, polymers with cationic groups, polymers with cationizable groups, cationically derivatized proteins, cationically derivatized protein hydrolyzates and betaine.

4. The hair-treating agent according to claim 3, wherein the cationic surfactants are compounds of formula (I)

$$N^{(+)}R^1R^2R^3R^4 X^{(-)} \tag{I}$$

wherein $R^1$ to $R^4$, independently of each other, each represent an aliphatic group, an aromatic group, an alkoxy group, a polyoxyalkylene group, an alkylamido group, a hydroxyalkyl group, an aryl group or an alkaryl group with 1 to 22 carbon atoms respectively, and $X^{(-)}$ stands for an anion.

5. The hair-treating agent according to claim 3, wherein the polymers with the cationic or the cationizable groups are selected from the group consisting of methylvinylimidazolium chloride/vinylpyrrolidone copolymers, quaternized vinylpyrrolidone/dimethyldiaminoethyl methacrylate copolymers, cationically derivatized polysaccharides, chitosan, chitosan salts and chitosan derivatives.

6. The hair-treating agent according to claim 1, wherein the hydrophobically modified aminoplast/polyether copolymers are copolymers of general formula (VI)

$$\tag{VI}$$

wherein Amp denotes an aminoplast monomer or a radical of an aminoplast oligomer or aminoplast polymer, AO denotes an alkylene oxide group, R denotes hydrogen, a $C_1$- to $C_4$-alkyl group or a $C_1$- to $C_4$-acyl and x and y are numbers greater than 1.

7. The hair-treating agent according to claim 1, wherein the hydrophobically modified aminoplast/polyether copolymers are reaction products of an acid-catalyzed reaction of a glycol uril derivative with a polyalkylene glycol and an alkoxylated hydrocarbon.

8. The hair-treating agent according to claim 1, wherein the hydrophobically modified aminoplast/polyether copolymers are polyether 1, PEG 180/Octoxynol 40/TMMG copolymer and PEG 180/Laureth 50/TMMG copolymer.

9. The hair-treating agent according to claim 1, wherein the hydrophobically modified aminoplast/polyether copolymers are in an optically clear form.

* * * * *